United States Patent
Ramin et al.

(10) Patent No.: US 6,228,349 B1
(45) Date of Patent: *May 8, 2001

(54) COMPOSITION COMPRISING MONOCARBOXYLIC ACID FOR TREATMENT OF KERATINOUS MATERIALS

(75) Inventors: Roland Ramin, Itteville; Jean-Claude Garson, Suresnes, both of (FR)

(73) Assignee: L'Oreal, Paris (FR)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/688,000

(22) Filed: Jul. 29, 1996

(30) Foreign Application Priority Data

Jul. 28, 1995 (FR) .................................... 9509251

(51) Int. Cl.⁷ .................................... A61K 7/043
(52) U.S. Cl. ..................... 424/61; 424/401; 514/784; 514/845; 514/846; 514/844
(58) Field of Search .................... 424/401, 61, 70.1; 514/784, 844, 845, 846, 871, 881

(56) References Cited

U.S. PATENT DOCUMENTS

| | | | |
|---|---|---|---|
| 2,729,586 | 1/1956 | Peck | 167/65 |
| 5,093,108 | * 3/1992 | Pappas et al. | 424/61 |
| 5,141,964 | * 8/1992 | Hugues | 514/777 |
| 5,443,855 | * 8/1995 | Wolf et al. | 424/401 |
| 5,484,586 | 1/1996 | Bedard | 424/61 |
| 5,792,447 | * 8/1998 | Socci et al. | 424/61 |
| 5,993,790 | * 8/1998 | Strauss | 424/61 |

FOREIGN PATENT DOCUMENTS

| | | |
|---|---|---|
| 0 102 534 | 8/1983 | (EP) . |
| 85/00288 | 7/1983 | (WO) . |
| 88/08701 | 5/1988 | (WO) . |

OTHER PUBLICATIONS

Schrader et al., "Grundlagen und Rezepturen der Kosmetika," pp. 730, 732, 737, 766 and 863 (no date) (with translation).

Jellinek et al., "Kosmetologie: Zweck und Aufbau kosmetischer Präparate," pp. 336–367, (1976) (with translation).

Navarre, "The Chemistry and Manufacture of Cosmetics," p. 113 (no date).

Schrader et al., "Grundlagen und Rezepturen der Kosmetika," pp. 477, 610 and 611 (1979) (with translation).

System Professional 3.9 Curl Stabilizer Trade Liturature by Wella (May 1995).

System Professional by Wella Price List (May 1995).

Literature from System Professional by Wella Press Conference (May 15/16 1995).

* cited by examiner

Primary Examiner—Thurman K. Page
Assistant Examiner—S. Howard
(74) Attorney, Agent, or Firm—Finnegan, Henderson, Farabow, Garrett & Dunner, L.L.P.

(57) ABSTRACT

A cosmetic composition comprising monocarboxylic acids for the treatment of keratinous materials, specially of the nails.

16 Claims, No Drawings

COMPOSITION COMPRISING MONOCARBOXYLIC ACID FOR TREATMENT OF KERATINOUS MATERIALS

The present invention relates to cosmetic compositions comprising carboxylic acids for the treatment of keratinous materials.

It is well known that the nails often exhibit defects in structure and in consistency, which may be diverse in their origin and related especially to the individual's internal functioning, to his or her living conditions, to his or her manner of feeding, to his or her age, and to his or her states of fatigue or of overwork.

These defects may also appear under the effect of actions which erode, for example as a result of prolonged or repeated exposures to detergents, to solvents, to chemical products, in particular those in household use, to moist or dry, hot or cold atmospheres or to exposures to UV radiations.

These defects in structure and consistency have the effect of making the surface of the nails unaesthetic, and this may be a source of embarrassment and of recurrent inconvenience.

With a view to strengthening the nails, various types of compositions have already been proposed, these being based essentially on the use either of agents which crosslink the proteins and are intended to strengthen the keratinous network, like, for example, formalin, or of agents the function of which is essentially nutritive, such as, for example, cystine, cholesterol, S-carboxymethylcysteine or extracts of collagen.

The use of such crosslinking agents or of such agents with a nutritive function does not, however, allow good results to be obtained and, furthermore, presents some disadvantages. In particular, formalin-based products can cause some allergic reactions.

The inventors have found that, by employing certain monocarboxylic acids, it is possible to obtain a remarkable hardening effect on the nails while avoiding the risks of intolerance and of sensitization.

The subject of the present invention is a cosmetic composition comprising at least one monocarboxylic acid preferably containing from 2 to 8 carbon atoms, and/or of one of its salts, as a hardening agent for keratinous materials, the acid containing no hydroxyl group.

Monocarboxylic acids containing from 2 to 5 carbon atoms may be more preferably employed.

The monocarboxylic acids according to the invention may be linear or branched. They may preferably be chosen from acetic acid, propionic acid, butyric acid, valeric acid, caproic acid, heptanoic acid or caprylic acid. Acetic acid is more preferably employed.

The monocarboxylic acid employed according to the invention may be a synthetic product. It may also be of natural origin.

Furthermore, the monocarboxylic acid employed according to the invention may preferably be introduced into the final composition in the form of free acid and/or in the form of one of its associated salts (especially salts with an organic base or an alkali).

According to the invention, the content of monocarboxylic acid may preferably range from 0.01% to 20% by weight and more preferably from 0.5% to 3%, relative to the total weight of the composition.

Furthermore, the cosmetic composition of the invention includes a cosmetically acceptable substrate.

This substrate may include organic solvents, water and/or is, for example, an oily medium.

Organic solvents which may be mentioned are ketones like acetone, methyl ethyl ketone and methyl isobutyl ketone, glycol ethers, alcohols like ethanol, n-butanol, n-propanol and isopropanol, acetates like butyl, ethyl, isopropyl acetate and 2-methoxyethyl acetate, linear or branched hydrocarbons such as hexane or octane, or else aromatic hydrocarbons such as xylene and toluene.

When the cosmetically acceptable support includes water, the composition may be presented especially in the form of an aqueous or hydroalcoholic solution, of an oil-in-water or water-in-oil emulsion or even of a multiple emulsion, or in the form of an aqueous gel.

The oily medium may include one or several volatile and/or nonvolatile oils, for example of vegetable, mineral, animal and/or synthetic origin, among which there may be mentioned:

animal or vegetable oils formed by esters of fatty acid and of polyols, in particular liquid triglycerides, for example sunflower, corn, soya, marrow, grape seed, sesame, hazelnut, apricot, almond or avocado oils, fish oils, glycerol tricaprocaprylate, or vegetable or animal oils of formula $R_1COOR_2$ in which $R_1$ denotes the residue of a higher fatty acid containing from 7 to 19 carbon atoms and $R_2$ denotes a branched hydrocarbon chain containing from 3 to 20 carbon atoms, for example Purcellin oil;

natural or synthetic essential oils such as, for example, eucalyptus, hybrid lavender, lavender, vetiver, lemon, sandal, rosemary, camomile, savory, nutmeg, cinnamon, hysop, caraway, orange, geraniol, cade and bergamot oils;

hydrocarbons such as hexadecane and liquid paraffin;

esters of mineral acid and of an alcohol;

ethers and polyethers;

silicone oils and gums.

In addition, the composition may include a film-forming polymer, and this makes it possible to deposit, for example on the nail, a strong film which ensures a prolonged contact of the monocarboxylic acid with the nail surface.

By way of example, the polymer may be chosen from nitrocellulose, cellulose acetobutyrate, polyvinylbutyral polymers, alkyd resins, polyesters, acrylics and polyurethanes.

The polymers may be dissolved or dispersed in the composition. They may be generally present in a concentration ranging from 1% to 40% by weight relative to the total weight of the composition.

In addition to the film-forming polymer the composition according to the invention may also include plasticizers which allow the flexibility of the film to be adjusted without weakening its physical strength.

The plasticizers that can be employed are those commonly employed in nail varnish compositions. Plasticizers which may be mentioned are dibutyl, dioctyl, diisobutyl and dimethoxyethyl phthalates, benzyl and glyceryl benzoates, triethyl and tributyl citrates, tributyl acetylcitrate, tributyl and triphenyl phosphates, glycols, camphor derivatives, and their mixtures. The plasticizers may be generally present in a concentration ranging from 1% to 30% by weight relative to the total weight of the composition.

Furthermore, the composition according to the invention may contain adjuvants which are commonly employed in cosmetic compositions. Adjuvants which may be mentioned by way of example are dyes, pigments, mothers-of-pearl, lacquers, anti-UV agents, thickening agents, surfactants, waxes, perfumes and active substances such as D-panthenol, phytantriol, vitamin derivatives, keratin derivatives, melanin, collagen, cystine, chitosan derivatives, ceramides, biotin, the oligoelements, glycerine, protein hydrolysates, phospholipids and hydrating agents.

A person skilled in the art will know how to choose this or these possible adjuvants and/or their quantity in such a way that the advantageous properties of the composition according to the invention are not, or substantially are not, impaired by the envisaged addition.

The keratinous materials treated with the composition according to the invention may be the nails, the eyelashes, the eyebrows and the hair.

The composition according to the invention may be in the form of a make-up composition such as a mascara, or of a hair-care composition, and finds a very particular application in the form of a composition to be applied to the nail, such as a nail varnish or a composition for nail care.

Examples illustrating the present invention will now be given without, however, limiting it.

EXAMPLE 1

The hardness of a nail treated with acetic acid was determined.

Principle

A penetrometer in the form of a square-based pyramid was applied to the nail with the aid of a load P. The average dimension of a diagonal of the square imprint obtained with the penetrometer was then determined.

The Vickers hardness (HV) was then determined by the relationship:

$HV = 1854.4 \times P/d^2$ d = mean diagonal in $\mu m$

P = applied loading

The measurement of the Vickers hardness was performed with the aid of the M 400 g 2 microdurometer from the Leco company.

Procedure

Fragments of nails were immersed in distilled water for 3 hours and were then left in the ambient moisture for 24 hours.

2 $\mu l$ of aqueous solution of acetic acid at a concentration of 10% by weight were then applied to the nail. The nails were then placed in an atmosphere of 75% relative humidity for 3 days. The measurement of the Vickers hardness was then performed.

A second application of the product and a second measurement of hardness were then performed according to the same conditions described above.

The test was conducted on three samples, in comparison with water (placebo).

Results

The following results were obtained:

| Treatment | Initial hardness without treatment | Hardness after the first application | Hardness after the second application |
|---|---|---|---|
| Water | 11.4 ± 0.6 | 10.7 ± 0.7 | 10.9 ± 0.2 |
| Acetic acid | 10.7 ± 0.7 | 12.5 ± 0.4 (+16.8%) | 11.9 ± 0.8 (+11.2%) |

The reported values correspond to the average obtained for three samples. The numbers shown in brackets show the increase in the hardness of the treated nail when compared with the nail before treatment.

It was found that the hardness of the nails increases appreciably after treatment with acetic acid.

These tests confirmed that acetic acid has the property of hardening the nail.

EXAMPLE 2

A colorless base which had the following composition was prepared:

| | |
|---|---|
| nitrocellulose | 15 g |
| plasticizer and resin | 15 g |
| isopropyl alcohol | 9 g |
| acetic acid | 1 g |
| solvent (ethyl acetate, butyl acetate) | q.s. 100 g |

After application of the composition to the nail and after drying a smooth and homogeneous film was obtained.

This composition was applied every 3 days to hard nails for 8 weeks. Before each application the old film is removed from the nails with the aid of a conventional dissolvent.

It was found that the nails thus treated were hardened.

We claim:

1. A composition comprising at least one compound, wherein said at least one compound is a monocarboxylic acid containing from 2 to 8 carbon atoms, wherein said monocarboxylic acid contains no hydroxyl group, wherein said monocarboxylic acid is present in an amount ranging from 0.5% to 20% by weight, relative to the total weight of the composition, and further wherein said composition is a hardening agent for nails.

2. A composition according to claim 1, wherein said monocarboxylic acid contains from 2 to 5 carbon atoms.

3. A composition according to claim 1, wherein said salt of said monocarboxylic acid is a salt with an organic base or with an alkali metal.

4. A composition according to claim 1, wherein said monocarboxylic acid is acetic acid, propionic acid, butyric acid, valeric acid, caproic acid, heptanoic acid or caprylic acid.

5. A composition according to claim 4, wherein said monocarboxylic acid is acetic acid.

6. A composition according to claim 1, wherein said monocarboxylic acid is present in an amount ranging from 0.5% to 3%, by weight relative to the total weight of the composition by weight.

7. A composition according to claim 1, wherein said composition further comprises at least one cosmetically acceptable substrate.

8. A composition according to claim 7, wherein said at least one cosmetically acceptable substrate is an organic solvent, water or oil.

9. A composition according to claim 1, wherein said composition further comprises at least one film-forming polymer, wherein said at least one film-forming polymer is a nitrocellulose, a cellulose acetobutyrate, a polyvinylbutyral compound, an alkyd resin, an acrylic or a polyurethane.

10. A composition according to claim 9, wherein said at least one film-forming polymer is present in a concentration ranging from 1 to 40% by weight, relative to the total weight of the composition.

11. A composition according to claim 1, wherein said composition further comprises at least one plasticizer.

12. A composition according to claim 11, wherein said at least one plasticizer is present in a concentration ranging from 1 to 30% by weight, relative to the total weight of the composition.

13. A composition according to claim 1, wherein said composition further comprises at least one adjuvant.

14. A composition according to claim 1, wherein said composition is a composition for nail care.

15. A composition according to claim 14, wherein said composition to be applied to the nail is a nail varnish or a composition for nail care.

16. A method for hardening a nail comprising the step of contacting said nail with an amount of a composition according to claim 1 effective for hardening.

* * * * *

UNITED STATES PATENT AND TRADEMARK OFFICE
CERTIFICATE OF CORRECTION

PATENT NO. : 6,228,349 B1
DATED : May 8, 2001
INVENTOR(S) : Roland Ramin et al.

It is certified that error appears in the above-identified patent and that said Letters Patent is hereby corrected as shown below:

<u>Title page,</u>
<u>Item [57], Abstract,</u>
Line 2, "specially" should read -- especially --.

Signed and Sealed this

Thirteenth Day of November, 2001

Attest:

NICHOLAS P. GODICI
Attesting Officer   Acting Director of the United States Patent and Trademark Office